(12) United States Patent
Zhou et al.

(10) Patent No.: US 11,292,809 B2
(45) Date of Patent: Apr. 5, 2022

(54) CRYSTALS OF GLYCYRRHIZIC ACID DERIVATIVES, CRYSTALLINE COMPOSITIONS, PHARMACEUTICAL COMPOSITIONS AND USES THEREOF

(71) Applicant: CHIA TAI TIANQING PHARMACEUTICAL GROUP CO., LTD., Jiangsu (CN)

(72) Inventors: Zhou Zhou, Jiangsu (CN); Wenwei Xu, Jiangsu (CN); Aiming Zhang, Jiangsu (CN); Xiquan Zhang, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 17/047,292

(22) PCT Filed: Apr. 12, 2019

(86) PCT No.: PCT/CN2019/082400
§ 371 (c)(1),
(2) Date: Oct. 13, 2020

(87) PCT Pub. No.: WO2019/196920
PCT Pub. Date: Oct. 17, 2019

(65) Prior Publication Data
US 2021/0317155 A1    Oct. 14, 2021

(30) Foreign Application Priority Data
Apr. 13, 2018  (CN) .......................... 201810331882.8

(51) Int. Cl.
*C07H 15/256*    (2006.01)

(52) U.S. Cl.
CPC ........ *C07H 15/256* (2013.01); *C07B 2200/13* (2013.01)

(58) Field of Classification Search
None
See application file for complete search history.

(56) References Cited

FOREIGN PATENT DOCUMENTS

| CN | 1381462 A | 11/2002 |
| CN | 1169826 C | 10/2004 |
| CN | 104861031 A | 8/2015 |

OTHER PUBLICATIONS

CN1169826C, Oct. 6, 2004, machine translation. (Year: 2004).*
International Search Report and Written Opinion for International Application No. PCT/CN2019/082400, State Intellectual Property Office of the P.R. China, China, dated May 30, 2019, 15 pages (with English Translation).

* cited by examiner

*Primary Examiner* — Layla D Berry
(74) *Attorney, Agent, or Firm* — Ping Wang; Rimon Law

(57) ABSTRACT

This application belongs to the field of pharmaceutical technology, and relates to the crystals of glycyrrhizic acid derivatives, their crystalline and pharmaceutical compositions, and medical use thereof, and, in particular, to the crystalline form A, crystalline form B, crystalline form C, crystalline form D, and crystalline form E of magnesium isoglycyrrhizinate, the method of preparing the crystals, the crystalline and pharmaceutical compositions containing the crystals, and medical use thereof. The crystalline forms prepared according to this application have overcome the defects of the compound of Formula I prepared according to the prior art, such as solid caking, difficult filtration, hard drying, and poor clarity. They are also suitable for industrial production, and capable of improving product safety.

20 Claims, 4 Drawing Sheets

CRYSTALS OF GLYCYRRHIZIC ACID DERIVATIVES, CRYSTALLINE COMPOSITIONS, PHARMACEUTICAL COMPOSITIONS AND USES THEREOF

CROSS-REFERENCE TO RELATED APPLICATIONS

This application claims priority and the benefits of Chinese Patent Application No. 201810331882.8 filed at the State Intellectual Property Office of the People's Republic of China on Apr. 13, 2018, the disclosure of which is incorporated herein by reference in their entirety.

TECHNICAL FIELD

This application belongs to the field of pharmaceutical technology, and relates to crystalline forms of glycyrrhizic acid derivatives, and, in particular, to the crystalline magnesium isoglycyrrhizinate, the preparation method thereof, the crystalline compositions and pharmaceutical compositions comprising the same, and medical uses thereof.

BACKGROUND

*Glycyrrhiza* is a commonly used medicinal plant, the main active ingredients of which are glycyrrhizic acids, i.e., 18-β glycyrrhizic acid and 18-α glycyrrhizic acid (also referred to as isoglycyrrhizic acid). Chinese Patent No. ZL02111693.8 discloses a new compound magnesium isoglycyrrhizinate (structure shown in Formula I, with a molecular weight of 845); Numerous pharmacological and biochemical studies have demonstrated that it can significantly inhibit serum transaminase elevation in animals, alleviate hepatocyte degeneration and necrosis and inflammatory cell infiltration, and promote hepatocyte regeneration in liver-injury animal models induced by different hepatotoxic agents, and effect of magnesium isoglycyrrhizinate against liver injury is obviously superior to that of natural glycyrrhizic acids.

Due to variations in crystalline forms, pharmaceutical compounds usually have different melting points, solubility, stability, and biological activity, all of which are important factors influencing the difficulty in drug preparation, the storage stability, the bioavailability, and the like. When a compound has polymorphs, it should be noted that a specified polymorph has its specific thermodynamic property and stability. Thus, it is important to understand the crystalline forms of a compound used in various dosage forms during preparation, so as to ensure that drugs of the same crystalline form are used in the manufacture. For this reason, it is necessary to ensure that a compound exists in a single crystalline form or mixture of some crystalline forms.

When determining which polymorph is preferable, their properties should be compared, and the preferable one is selected based on several physical properties. It is entirely possible that one polymorph is preferable on the condition that some properties such as difficulty in drug preparation and stability are considered critical. Under other circumstances, another polymorph may be preferable for its higher solubility or outstanding pharmacokinetic property.

The discovery of new polymorphs of a pharmaceutical compound offers opportunities to improve the physical properties, that is, to extend all properties, and better guide the research of the compound and its preparations. When several polymorphs are discovered, it is required to carefully examine the conditions for the preparation of each polymorph. In this way, certain crystallization conditions can be maintained between batches, thus ensuring that active pharmaceutical ingredients and pharmaceutical preparations thereof have uniform and consistent crystalline form. The changes in recrystallization solvent, crystallization rate or other factors may cause one crystalline form to be predominant. Thus, the crystalline forms of the isoglycyrrhizinate salts and the pharmaceutical compositions thereof provided in this application have commercial value in drug manufacturing and other applications.

SUMMARY OF THE INVENTION

In the first aspect, this application provides a crystalline form A of the compound of Formula I (hereinafter referred to as "crystalline form A"), using Cu-Kα radiation, the crystalline form A has an X-ray powder diffraction (XRD) pattern comprising diffraction peaks at 2θ value (°) of about 3.57, 7.10, 13.83, 14.65 and 15.48.

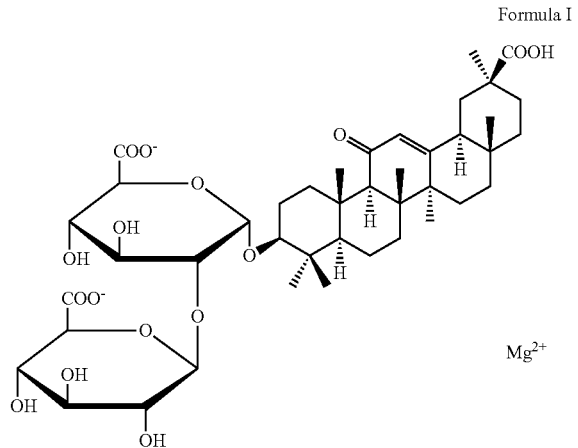
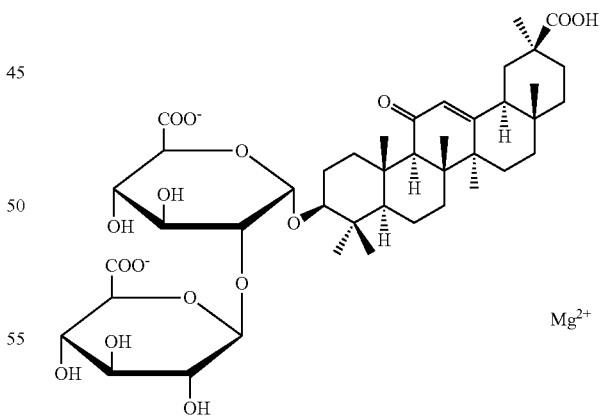

Formula I

Typically, the crystalline form A comprises diffraction peaks at 2θ value (°) of about 3.57, 7.10, 12.20, 13.83, 14.65, 15.48, 17.00 and 17.80.

More typically, the crystalline form A comprises diffraction peaks at 2θ value (°) of about 3.57, 7.10, 10.66, 12.20, 13.83, 14.04, 14.13, 14.65, 15.48, 17.00, 17.80 and 19.46.

In some embodiments, the crystalline form A contains 7.0~10.0% (wt %) water by weight; in some embodiments, it contains 7.2~9.0% (wt %) water by weight; in some specific embodiments, it contains 7.7~8.8% (wt %) water by weight.

In some specific embodiments, a crystalline form A containing four moles of water is provided. In some specific embodiments, the crystalline form A of the present application is a tetrahydrate of the compound of Formula I.

In a specific embodiment, using Cu-Kα radiation, a typical XRD spectrum of crystalline form A has the following characteristics:

| No. | 2θ (°) | d value (Å) | Relative intensity (%) |
|---|---|---|---|
| 1 | 3.57 | 24.74 | 100.0 |
| 2 | 7.10 | 12.45 | 22.6 |
| 3 | 10.66 | 8.29 | 4.5 |
| 4 | 12.20 | 7.25 | 5.9 |
| 5 | 13.83 | 6.40 | 18.5 |
| 6 | 14.04 | 6.30 | 13.4 |
| 7 | 14.13 | 6.26 | 6.8 |
| 8 | 14.65 | 6.04 | 14.0 |
| 9 | 15.19 | 5.83 | 3.3 |
| 10 | 15.48 | 5.72 | 27.0 |
| 11 | 17.00 | 5.21 | 5.8 |
| 12 | 17.80 | 4.98 | 8.8 |
| 13 | 18.41 | 4.82 | 2.9 |
| 14 | 19.46 | 4.56 | 3.4 |

In a specific embodiment, the crystalline form A of the compound of Formula I substantially has the X-ray powder diffraction pattern of FIG. 1.

In a particular embodiment, the thermogravimetry-derivative thermogravimetry (TG-DTG) spectrum of the crystalline form A is as shown in FIG. 2, which shows a weight loss of 8.74% (about 4 moles of water).

In some embodiments, the crystalline form A has a specific surface area of ≤1.0 $m^2/cm^3$; in some embodiments, it has a specific surface area of ≤0.5 $m^2/cm^3$. In a specific embodiment, the crystalline form A has a specific surface area of about 0.4 $m^2/cm^3$.

In some embodiments, the crystalline form A has a specific surface area of ≤1.0 $m^2/g$; in some embodiments, it has a specific surface area of ≤0.8 $m^2/g$; in some embodiments, it has a specific surface area of ≤0.7 $m^2/g$. In a specific embodiment, the crystalline form A has a specific surface area of about 0.6 $m^2/g$.

In some embodiments, the crystalline form A has a particle size distribution characterized as follows: (i) an X10 value of about 3~10 μm, or an X10 value of 5~8 μm, or an X10 value of 6~6.5 μm; (ii) an X50 value of about 30~55 μm, or an X50 value of 40~47 μm, or an X50 value of 42~45 μm; or (iii) an X90 value of about 80~120 μm, or an X90 value of 90~100 μm, or an X90 value of 91~98.5 μm; or any combination of two or more of (i), (ii), and (iii). In some embodiments, its particle size distribution is characterized by an X10 value of 6~6.5 μm, an X50 value of 42~45 μm, an X90 value of 91~98.5 μm.

In the second aspect, this application provides a crystalline form B of the compound of Formula I (hereinafter referred to as "crystalline form B"), when using Cu-Kα radiation, the crystalline form B has an X-ray powder diffraction (XRD) pattern comprising diffraction peaks at 2θ value (°) of about 4.09, 7.95, 11.82, 14.71, 15.71, 19.64, 23.55 and 27.51.

Typically, the crystalline form B comprises diffraction peaks at 2θ value (°) of about 3.97, 4.09, 7.95, 11.82, 12.97, 14.71, 15.71, 16.63, 19.64, 21.67, 23.55 and 27.51.

More typically, the crystalline form B comprises diffraction peaks at 2θ value (°) of about 3.97, 4.09, 7.95, 11.11, 11.82, 12.97, 13.59, 14.71, 15.71, 16.18, 16.63, 17.96, 19.64, 21.67, 23.55, 27.51 and 31.50.

In some embodiments, the crystalline form B contains 0~20% (wt %) ethanol by weight and/or 9.0~20.0% (wt %) water by weight.

In some embodiments, it contains 9.5~10.5% (wt %) water by weight. In some embodiments, it contains 10.5~11.5% (wt %) water by weight. In some embodiments, it contains 11.5~13.5% (wt %) water by weight. In some embodiments, it contains 13.5~15.5% (wt %) water by weight. In some embodiments, it contains 15.5~16.5% (wt %) water by weight. In some embodiments, it contains 16.5~18.0% (wt %) water by weight.

In a specific embodiment, this application provides a crystalline form B of the compound of Formula I containing 5~10 moles of water. In some embodiments, the crystalline form B is pentahydrate; in some embodiments, the crystalline form B is hexahydrate; in some embodiments, the crystalline form B is heptahydrate; in some embodiments, the crystalline form B is octahydrate; in some embodiments, the crystalline form B is nonahydrate; in some embodiments, the crystalline form B is decahydrate.

In a specific embodiment, using Cu-Kα radiation, a typical XRD spectrum of the crystalline form B has the following characteristics:

| No. | 2θ (°) | d value (Å) | Relative intensity (%) |
|---|---|---|---|
| 1 | 3.97 | 22.24 | 4.2 |
| 2 | 4.09 | 21.60 | 100.0 |
| 3 | 7.42 | 11.90 | 0.6 |
| 4 | 7.95 | 11.11 | 12.4 |
| 5 | 11.11 | 7.96 | 0.8 |
| 6 | 11.82 | 7.48 | 11.2 |
| 7 | 12.73 | 6.95 | 0.3 |
| 8 | 12.97 | 6.82 | 0.9 |
| 9 | 13.59 | 6.51 | 0.6 |
| 10 | 14.71 | 6.02 | 4.0 |
| 11 | 15.71 | 5.64 | 11.3 |
| 12 | 16.18 | 5.47 | 0.7 |
| 13 | 16.63 | 5.33 | 1.8 |
| 14 | 17.26 | 5.13 | 0.2 |
| 15 | 17.96 | 4.94 | 0.5 |
| 16 | 19.64 | 4.52 | 5.2 |
| 17 | 20.35 | 4.36 | 0.1 |
| 18 | 20.86 | 4.26 | 0.3 |
| 19 | 21.67 | 4.10 | 1.1 |
| 20 | 22.08 | 4.02 | 0.2 |
| 21 | 23.55 | 3.77 | 7.6 |
| 22 | 24.55 | 3.77 | 0.1 |
| 23 | 25.37 | 3.51 | 0.3 |
| 24 | 27.25 | 3.27 | 0.2 |
| 25 | 27.51 | 3.24 | 8.0 |
| 26 | 31.50 | 2.81 | 1.3 |

In a specific embodiment, the crystalline form B of the compound of Formula I substantially has the X-ray powder diffraction pattern of FIG. 3.

In the third aspect, this application provides a crystalline form C of the compound of Formula I (hereinafter referred to as "crystalline form C"), when using Cu-Kα radiation, the crystalline form C has an X-ray powder diffraction (XRD) pattern comprising diffraction peaks at 2θ value (°) of about 3.68, 3.95, 7.17, 7.29, 7.85, 11.72, 15.60, 16.51, 19.57, 23.47 and 27.42.

Typically, the crystalline form C comprises diffraction peaks at 2θ value (°) of about 3.68, 3.93, 3.95, 7.17, 7.29, 7.85, 11.02, 11.72, 14.58, 15.60, 16.06, 16.51, 19.57, 23.47 and 27.42.

More typically, the crystalline form C comprises diffraction peaks at 2θ value (°) of about 3.68, 3.93, 3.95, 7.17, 7.29, 7.85, 11.02, 11.72, 14.58, 15.60, 16.06, 16.51, 17.84, 19.57, 23.47, 27.42 and 31.79.

In some embodiments, the crystalline form C contains 10.0~17.0% (wt %) water by weight; in some embodiments, the crystalline form C contains 10.0~14.0% (wt %) water by weight; in some embodiments, it contains 10.5~11.5% (wt %) water by weight. In some embodiments, it contains 11.5~12.8% (wt %) water by weight. In some embodiments, it contains 12.8~13.5% (wt %) water by weight. In some specific embodiments, it contains 14.5~14.9% (wt %) water by weight. In some embodiments, it contains 16.0~16.3% (wt %) water by weight. In some embodiments, it contains 14.9~16.0% (wt %) water by weight. In a specific embodiment, it contains 15.6% (wt %) water by weight. In a specific embodiment, it contains 11.1% (wt %) water by weight.

In a specific embodiment, a crystalline form C of the compound of Formula I containing 6~9 moles of water is provided. In some embodiments, the crystalline form C is hexahydrate; in some embodiments, the crystalline form C is heptahydrate; in some embodiments, the crystalline form C is octahydrate; in some embodiments, the crystalline form C is nonahydrate.

In a specific embodiment, using Cu-Kα radiation, a typical XRD spectrum of the crystalline form C has the following characteristics:

| No. | 2θ (°) | d value (Å) | Relative intensity (%) |
|---|---|---|---|
| 1 | 3.68 | 24.01 | 25.5 |
| 2 | 3.93 | 22.46 | 76.1 |
| 3 | 3.95 | 22.35 | 100.0 |
| 4 | 7.17 | 12.32 | 5.5 |
| 5 | 7.29 | 12.12 | 4.2 |
| 6 | 7.85 | 11.26 | 37.5 |
| 7 | 10.63 | 8.31 | 2.8 |
| 8 | 11.02 | 8.03 | 6.1 |
| 9 | 11.72 | 7.54 | 35.9 |
| 10 | 12.89 | 6.87 | 3.9 |
| 11 | 13.52 | 6.55 | 5.2 |
| 12 | 13.89 | 6.37 | 3.1 |
| 13 | 14.13 | 6.26 | 4.4 |
| 14 | 14.58 | 6.07 | 17.2 |
| 15 | 15.60 | 5.68 | 39.2 |
| 16 | 16.06 | 5.52 | 8.0 |
| 17 | 16.51 | 5.36 | 34.0 |
| 18 | 17.84 | 4.97 | 3.8 |
| 19 | 19.12 | 4.64 | 2.8 |
| 20 | 19.57 | 4.32 | 26.5 |
| 21 | 20.74 | 4.28 | 2.3 |
| 22 | 21.52 | 4.13 | 3.2 |
| 23 | 23.47 | 3.79 | 36.6 |
| 24 | 23.71 | 3.75 | 2.2 |
| 25 | 25.27 | 3.52 | 3.3 |
| 26 | 27.42 | 3.25 | 38.5 |
| 27 | 31.41 | 2.85 | 5.7 |
| 28 | 31.79 | 2.81 | 10.9 |

In a specific embodiment, the crystalline form C of the compound of Formula I basically has the X-ray powder diffraction pattern of FIG. 4.

In the fourth aspect, this application provides a crystalline form D of the compound of Formula I (hereinafter referred to as "crystalline form D"), wherein using Cu-Kα radiation, the crystalline form D has an X-ray powder diffraction (XRD) pattern comprising diffraction peaks at 2θ value (°) of about 3.66, 3.99, 7.18, 7.85, 10.72, 11.72, 15.57, 17.85, 19.56, 23.45 and 27.40.

Typically, the crystalline form D comprises diffraction peaks at 2θ value (°) of about 3.66, 3.99, 7.18, 7.85, 10.72, 11.72, 12.26, 13.91, 14.22, 14.69, 15.57, 17.85, 19.56, 23.45 and 27.40.

In some embodiments, the crystalline form D contains 8.5~11.5% (wt %) water by weight. In some embodiments, it contains 9.0~9.8% (wt %) water by weight. In some embodiments, it contains 11.1~11.5% (wt %) water by weight. In some embodiments, it contains 9.8~11.1% (wt %) water by weight. In a specific embodiment, it contains 10.1% (wt %) water by weight.

In a specific embodiment, a crystalline form D of the compound of Formula I containing 5~6 moles of water is provided. In some embodiments, the crystalline form D is pentahydrate; in some embodiments, the crystalline form D is hexahydrate.

In a specific embodiment, using Cu-Kα radiation, a typical XRD spectrum of the crystalline form D has the following characteristics:

| No. | 2θ (°) | d value (Å) | Relative intensity (%) |
|---|---|---|---|
| 1 | 3.66 | 24.15 | 100 |
| 2 | 3.99 | 22.14 | 52.5 |
| 3 | 7.18 | 12.30 | 17.8 |
| 4 | 7.85 | 11.25 | 5.7 |
| 5 | 10.72 | 8.25 | 4.2 |
| 6 | 11.72 | 7.54 | 6.3 |
| 7 | 12.26 | 7.22 | 1.8 |
| 8 | 12.89 | 6.87 | 1.1 |
| 9 | 13.50 | 6.55 | 1.5 |
| 10 | 13.91 | 6.36 | 4.9 |
| 11 | 14.22 | 6.22 | 4.0 |
| 12 | 14.69 | 6.02 | 6.0 |
| 13 | 15.23 | 5.81 | 1.4 |
| 14 | 15.57 | 5.69 | 16.1 |
| 15 | 17.08 | 5.19 | 2.7 |
| 16 | 17.85 | 4.96 | 9.5 |
| 17 | 19.56 | 4.54 | 3.9 |
| 18 | 19.66 | 4.51 | 1.6 |
| 19 | 23.45 | 3.79 | 5.4 |
| 20 | 27.40 | 3.25 | 7.0 |
| 21 | 31.39 | 2.84 | 1.0 |

In a specific embodiment, the crystalline form D of the compound of Formula I basically has the X-ray powder diffraction pattern of FIG. 6.

In the fifth aspect, this application provides a crystalline form E of the compound of Formula I (hereinafter referred to as "crystalline form E"), wherein, using Cu-Kα radiation, the crystalline form E has an X-ray powder diffraction (XRD) pattern comprising diffraction peaks at 2θ value (°) of about 3.78, 11.23, 11.86, 12.72, and 18.53.

Typically, the crystalline form E comprises diffraction peaks at 2θ value (°) of about 3.78, 9.46, 11.23, 11.86, 12.72, 17.02, 17.30 and 18.53.

More typically, the crystalline form E comprises diffraction peaks at 2θ value (°) of about 3.78, 9.46, 11.23, 11.86, 12.72, 13.58, 17.02, 17.30, 18.53, 19.08 and 20.43.

In some embodiments, crystalline form E contains 7.0~20.0% (wt %) water by weight. In some embodiments, it contains 7.5~9.5% (wt %) water by weight. In some embodiments, it contains 9.5~10.5% (wt %) water by weight. In some embodiments, it contains 10.5~11.5% (wt %) water by weight. In some embodiments, it contains 11.5~13.5% (wt %) water by weight. In some embodiments, it contains 13.5~15.5% (wt %) water by weight.

In a specific embodiment, a crystalline form E of the compound of Formula I containing 4~8 moles of water is provided. In some embodiments, the crystalline form E is tetrahydrate; in some embodiments, the crystalline form E is pentahydrate; in some embodiments, the crystalline form E is hexahydrate; in some embodiments, the crystalline form E is heptahydrate; in some embodiments, the crystalline form E is octahydrate.

In a specific embodiment, using Cu-Kα radiation, a typical XRD spectrum of the crystalline form E has the following characteristics:

| No. | 2θ (°) | d value (Å) | Relative intensity (%) |
|-----|--------|-------------|------------------------|
| 1   | 3.78   | 23.37       | 100.0%                 |
| 2   | 9.46   | 9.34        | 4.5%                   |
| 3   | 11.23  | 7.87        | 21.8%                  |
| 4   | 11.86  | 7.46        | 20.6%                  |
| 5   | 12.72  | 6.95        | 10.5%                  |
| 6   | 13.58  | 6.52        | 7.7%                   |
| 7   | 17.02  | 5.21        | 8.0%                   |
| 8   | 17.30  | 5.12        | 8.5%                   |
| 9   | 18.53  | 4.78        | 14.7%                  |
| 10  | 19.08  | 4.65        | 6.5%                   |
| 11  | 20.43  | 4.34        | 4.5%                   |

In a specific embodiment, the crystalline form E of the compound of Formula I basically has the X-ray powder diffraction pattern of FIG. 7.

In the sixth aspect, this application provides a crystalline form of the compound of the formula I, which has a specific surface area of ≤1.0 m$^2$/cm$^3$. In some embodiments, it has a specific surface area of ≤0.5 m$^2$/cm$^3$, and the crystalline form can be, for example, the crystalline form A, crystalline form B, crystalline form C, or crystalline form D, or any combination of two or more of them.

This application also provides a crystalline form of the compound of the formula I having a specific surface area of ≤1.0 m$^2$/g; in some embodiments, it has a specific surface area of ≤0.8 m$^2$/g; in some embodiments, it has a specific surface area of ≤0.7 m$^2$/g. In a specific embodiment, a crystalline form of the compound of the formula I has a specific surface area of about 0.6 m$^2$/g; the crystalline form can be, for example, the crystalline form A, crystalline form B, crystalline form C, or crystalline form D, or any combination of two or more of them.

In some embodiments, a crystalline form of the compound of the formula I includes the crystalline form A, crystalline form B, crystalline form C, or crystalline form D, or any combination of two or more of them.

In some embodiments, the crystalline form has a particle size distribution characterized as follows: (i) an $X_{10}$ value of about 3~10 μm, preferably an $X_{10}$ value of 5~8 μm, more preferably an $X_{10}$ value of 6~6.5 μm; (ii) an $X_{50}$ value of about 30~55 μm, preferably an $X_{50}$ value of 40~47 μm, more preferably an $X_{50}$ value of 42~45 μm; or (iii) an $X_{90}$ value of about 80~120 μm, preferably an $X_{90}$ value of 90~100 μm, more preferably an $X_{90}$ value of 91~98.5 μm; or any combination of two or more of (i), (ii), and (iii). In some embodiments, its particle size distribution is characterized by an $X_{10}$ value of 6~6.5 μm, an $X_{50}$ value of 42~45 μm, an $X_{90}$ value of 91~98.5 μm.

In the seventh aspect, this application provides a method of preparing a crystalline form of the compound of the formula I, characterized in that:

(1) The compound of the formula I is mixed with a solvent, and the mixture is heated to obtain a solution;

(2) The solution is allowed to cool down gradually to obtain a crystalline form;

(3) A crystalline form is obtained through filtration and separation.

Wherein, activated carbon can be optionally added in step (1) before filtration of the solution while hot; in some embodiments, the solvent is a mixture of an organic solvent (including but not limited to ethanol and isopropanol) and water, such as ethanol/water. In some embodiments, the volume ratio (v/v) of the organic solvent to water is 0.5~2:1, preferably 1:1; in some embodiments, the mass ratio (m/m) of the organic solvent to water is 1~2:1, preferably 1.2~1.5:1. In some embodiments, the mass volume ratio (m/v) of the compound of the formula I to the solvent is 1:8~12, preferably 1:10. In some embodiments, the mixture is heated until reflux to obtain the solution of the compound of the formula I.

In some embodiments of step (2), the solution prepared in step (1) is cooled to a certain temperature, and then the mixture obtained is allowed to gradually cool down to obtain the crystalline form; in some embodiments, first the solution prepared in step (1) is cooled to 60~70° C. and maintained at this temperature for a period of time, and then the mixture obtained is allowed to gradually cool down to obtain the crystalline form; in some embodiments, first the solution prepared in step (1) is cooled to 60~70° C. and maintained at this temperature for about 4~20 h, preferably cooled to 60~70° C. and maintained at this temperature for about 6~12 h, and then the mixture obtained is allowed to gradually cool down to obtain the crystalline form. In some embodiments, the crystalline form is obtained through stirring. In some embodiments, the gradual cooling process means to decrease the temperature by 5~25° C. each time and maintain at each decreased temperature for a period of time (such as 2~20 h). In some embodiments, the gradual cooling process includes: the temperature is decreased by 5° C., 10° C., 15° C., 20° C., and/or 25° C. each time, and then maintained for 2~20 h; in some embodiments, the mixture is cooled successively to one or several of the temperature ranges 65~70° C., 60~65° C., 55~60° C., 50~55° C., 45~50° C., 40~45° C., 30~40° C., 20~30° C., 10~20° C., and 5~10° C., and then maintained for a period of time. In some embodiments, the mixture is finally cooled to −10° C.~10° C.; in some embodiments, the mixture is finally cooled to 0° C.~5° C. In some embodiments, a seed crystal is added to obtain the crystalline form; in some embodiments, there is no need to add a seed crystal.

In step (3), a solvent can be further used for cleansing in separation; in some embodiments, the solvent used for cleansing is a mixed solvent of ethanol/water. In some embodiments, the crystalline form can be obtained through separation; in some embodiments, optionally, the crystalline form obtained through separation can be further dried; in some embodiments, it is dried at 50~80° C.; in some embodiments, it is dried at 50~65° C.; in some embodiments, it is dried at about 60° C.; in some embodiments, the drying period lasts for 4~24 h; in some specific embodiments, the drying period lasts for 4~12 h, or 5~10 h; in some specific embodiments, the drying period lasts for 12~15 h, such as 14 h; in some specific embodiments, the drying period lasts for 15~24 h; in some embodiments, the drying period lasts for 18~20 h.

In some particular embodiments, this application provides a method of preparing a crystalline form of the compound of the formula I, characterized in that:

(1) the compound of the formula I is mixed with a mixed solvent of ethanol/water, and the mixture is heated until reflux to obtain a solution;

(2) the resulting solution is cooled to 60~70° C. and maintained at this temperature for about 4~20 h, then the mixture obtained is allowed to gradually cool down to obtain a crystalline form;

(3) a crystalline form is obtained through filtration and separation.

wherein activated carbon can be optionally added in step (1) before filtration of the solution while hot; in some embodiments of step (1), the volume ratio (v/v) of ethanol to water is 0.5~2:1, preferably 1:1. In some embodiments, the mass volume ratio (m/v) of the compound of the formula I to the mixed solvent is 1:8~12, preferably 1:10.

In some embodiments of step (2), first the solution prepared in step (1) is cooled to 60~70° C. and maintained at this temperature for about 6~12 h, and then the mixture obtained is allowed to gradually cool down to obtain the crystalline form. In some embodiments, the crystalline form is obtained through stirring. In some embodiments, the gradually cooling means to decrease the temperature by 5~25° C. each time and maintain at this decreased temperature for a period of time (such as 2~20 h). In some embodiments, during the gradually cooling, the temperature is decreased by 5° C., 10° C., 15° C., 20° C., and/or 25° C. each time, and then the temperature is maintained for 2~20 h; in some embodiments, during the gradually cooling, the mixture is cooled successively to one or several of the temperature ranges 65~70° C., 60~65° C., 55~60° C., 50~55° C., 45~50° C., 40~45° C., 30~40° C., 20~30° C., 10~20° C., and 5~10° C., and then maintained for 2~20 h. In some embodiments, the mixture is finally cooled to −10° C.~ 10° C.; in some embodiments, the mixture is finally cooled to 0° C.~5° C. In some embodiments, there is no need to add a seed crystal; in some embodiments, a seed crystal is added to obtain the crystalline form.

In step (3), a solvent can be further used for cleansing in separation; in some embodiments, the solvent used for cleansing is a mixed solvent of ethanol/water. In some embodiments, a crystalline form can be obtained through separation; in some embodiments, optionally, the crystalline form obtained through separation can be further dried; in some embodiments, it is dried at 50~80° C.; in some embodiments, it is dried at 50~65° C.; in some embodiments, it is dried at about 60° C.; in some embodiments, the drying period lasts for 4~24 h; in some specific embodiments, the drying period lasts for 4~12 h, or 5~10 h; in some specific embodiments, the drying period lasts for 12~15 h, such as 14 h; in some specific embodiments, the drying period lasts for 15~24 h; in some embodiments, the drying period lasts for 18~20 h.

In some embodiments of the seventh aspect, the crystalline form of the compound of formula I can be crystalline form A, crystalline form B, crystalline form C, crystalline form D, or crystalline form E, or any combination of two or more of them.

In some embodiments of the seventh aspect, the crystalline form has a specific surface area of ≤1.0 m²/cm³, or a specific surface area of ≤0.5 m²/cm³. In some embodiments, the crystalline form has a specific surface area of ≤1.0 m²/g, or a specific surface area of ≤0.8 m²/g, or a specific surface area of ≤0.7 m²/g. In a specific embodiment, the crystalline form A has a specific surface area of about 0.6 m²/g.

In some embodiments of the seventh aspect, the crystalline form has a particle size distribution characterized as follows: (i) an $X_{10}$ value of about 3~10 μm, preferably an $X_{10}$ value of 5~8 μm, and more preferably an $X_{10}$ value of 6~6.5 μm; (ii) an $X_{50}$ value of about 30~55 μm, preferably an $X_{50}$ value of 40~47 μm, and more preferably an $X_{50}$ value of 42~45 μm; or (iii) an $X_{90}$ value of about 80~120 μm, preferably an $X_{90}$ value of 90~100 μm, and more preferably an $X_{90}$ value of 91~98.5 μm; or any combination of two or more of (i), (ii), and (iii). In some embodiments, its particle size distribution is characterized by an $X_{10}$ value of 6~6.5 μm, an $X_{50}$ value of 42~45 μm, an $X_{90}$ value of 91~98.5 μm.

In some specific embodiments, the crystalline form obtained through separation in step (3) is dried at 50~80° C. for 15~24 h to obtain the crystalline form A. In some specific embodiments, the crystalline form obtained through separation in step (3) is dried at 55~65° C. for 18~20 h to obtain the crystalline form A. In some specific embodiments, the crystalline form obtained through separation in step (3) is dried at about 60° C. for 18~20 h to obtain the crystalline form A.

In some specific embodiments, separation can be performed in step (3) to obtain the crystalline form B.

In some specific embodiments, the crystalline form obtained through separation in step (3) is dried at 50~80° C. for 4~12 h, or 5~10 h to obtain the crystalline form C. In some specific embodiments, the crystalline form obtained through separation in step (3) is dried at 55-65° C. for 4~12 h or 5~10 h to obtain the crystalline form C. In some specific embodiments, the crystalline form obtained through separation in step (3) is dried at about 60° C. for 5~10 h to obtain the crystalline form C.

In some specific embodiments, the crystalline form obtained through separation in step (3) is dried at 50~80° C. for 12~15 h, or 14 h to obtain the crystalline form D. In some specific embodiments, the crystalline form obtained through separation in step (3) is dried at 55-65° C. for 12~15 h, such as 14 h, to obtain the crystalline form D. In some specific embodiments, the crystalline form obtained through separation in step (3) is dried at about 60° C. for 12~15 h, such as 14 h, to obtain the crystalline form D.

In addition, the crystalline form A can also be prepared with the crystalline form B. In some embodiments, the crystalline form B is dried at 50~80° C. for 15~24 h to obtain the crystalline form A; in a particular embodiment, the crystalline form B is dried at 55-65° C. for 15~24 h, or 18~20 h to obtain the crystalline form A; in a particular embodiment, the crystalline form B is dried at about 60° C. for 15~24 h, or 18~20 h to obtain the crystalline form A.

Additionally, the crystalline form A can also be prepared with the crystalline form C. In some embodiments, the crystalline form C is dried at 50~80° C. for 5~19 h to obtain the crystalline form A; in a particular embodiment, the crystalline form C is dried at 55-65° C. for 12~19 h, or at 55-65° C. for 13~15 h to obtain the crystalline form A; in a particular embodiment, the crystalline form C is dried at 55-65° C. for 5~12 h, or 55-65° C. for 8~11 h to obtain the crystalline form A.

Furthermore, the crystalline form A can also be prepared with the crystalline form D. In some embodiments, crystalline form D is dried at 50~80° C. for 1~10 h to obtain the crystalline form A; in a particular embodiment, crystalline form D is dried at 55-65° C. for 1~10 h, or 4~6 h to obtain the crystalline form A; in a particular embodiment, the crystalline form D is dried at about 60° C. for 1~10 h, or 4~6 h to obtain the crystalline form A.

In some particular embodiments, this application provides a method of preparing the crystalline form E of the compound of the formula I, characterized in that:

(1) The compound of formula I is mixed with a mixed solvent of isopropanol/water, and the mixture is heated until reflux to obtain a solution;

(2) the solution prepared in step (1) is cooled to 60~70° C. and maintained at this temperature for 4~20 h, and gradually cool down to obtain a crystalline form;

(3) a crystalline form is obtained through filtration and separation.

wherein activated carbon can be optionally added in step (1) before filtration of the solution while hot; in some embodiments of step (1), the mass ratio (m/m) of isopropanol to water is 1~2:1, preferably 1.2~1.5:1. In some embodiments of step (2), first the solution prepared in step (1) is cooled to 60~70° C. and maintained at this temperature for about 6~12 h, and then the mixture obtained is allowed to gradually cool down to obtain the crystalline form. In some embodiments, the crystalline form is obtained through stirring; in some embodiments, the gradually cooling means to decrease the temperature by 5~25° C. each time and maintain at this decreased temperature for a period of time, such as 2~20 h. In some embodiments, during the gradually cooling, the temperature is decreased by 5° C., 10° C., 15° C., 20° C., and/or 25° C. each time, and then maintained for 2~20 h; in some embodiments, the mixture is cooled successively to one or several of the temperature ranges 65~70° C., 60~65° C., 55~60° C., 50~55° C., 45~50° C., 40~45° C., 30~40° C., 20~30° C., 10~20° C., and 5~10° C., and then maintained for 2~20 h. In some embodiments, the mixture is finally cooled to −10° C.~ 10° C.; in some embodiments, the mixture is finally cooled to 0° C.~5° C. In some embodiments, there is no need to add a crystal. In some embodiments, a seed crystal is added to obtain crystalline form.

In step (3), a solvent can be further used for cleansing in separation; in some embodiments, the solvent used for cleansing is a mixed solvent of isopropanol/water; in some embodiments, separation can be performed to obtain crystalline form E; in some embodiments, optionally, the crystalline form obtained through separation can be further dried to obtain crystalline form E; in some embodiments, it is dried at 50~80° C. or at 55-65° C. In some embodiments, it is dried at about 60° C.; in a particular embodiment, the drying period lasts for 10~12 h.

In the eighth aspect, this application provides a crystalline composition of crystalline form A, crystalline form B, crystalline form C, crystalline form D, or crystalline form E, wherein the crystalline composition of the crystalline form A refers to a composition in which the crystalline form A accounts for above 50% by weight of the composition, or above 70%, or above 90%, or above 95%. The composition may contain a small amount of other crystalline form or amorphous form of the compound of Formula I.

The crystalline composition of the crystalline form B refers to a composition in which the crystalline form B accounts for above 50% by weight of the composition, or above 70%, or above 90%, or above 95%. The composition may contain a small amount of other crystalline form or amorphous form of the compound of the formula I.

The crystalline composition of the crystalline form C refers to a composition in which the crystalline form C accounts for above 50% by weight of the composition, or above 70%, or above 90%, or above 95%. The composition may contain a small amount of other crystalline form or amorphous form of the compound of the formula I.

The crystalline composition of the crystalline form D refers to a composition in which the crystalline form D accounts for above 50% by weight of the composition, or above 70%, or above 90%, or above 95%. The composition may contain a small amount of other crystalline form or amorphous form of the compound of the formula I.

The crystalline composition of the crystalline form E refers to a composition in which the crystalline form E accounts for above 50% by weight of the composition, or above 70%, or above 90%, or above 95%. The composition may contain a small amount of other crystalline form or amorphous form of the compound of the formula I.

For the purpose of this application, the crystalline form A or its crystalline composition, the crystalline form B or its crystalline composition, the crystalline form C or its crystalline composition, the crystalline form D or its crystalline composition, and the crystalline form E or its crystalline composition are hereinafter collectively referred to as "the active ingredient of this application".

The active ingredient of this application can be administered by any route suitable to the disease under treatment, including oral administration, topical administration (such as oral administration and sublingual administration), parenteral administration (such as subcutaneous administration, intramuscular administration, intravenous administration, spinal cord administration, endermic administration, and intrathecal administration), rectal administration, vaginal administration, etc. The preferable route of administration is intravenous infusion (dropwise).

In another aspect, this application provides pharmaceutical compositions, which include the crystalline form A, crystalline form B, crystalline form C, crystalline form D, or crystalline form E, or their crystalline compositions.

Although the active ingredient of this application can be administered without other ingredients, it is usually administered in the form of a pharmaceutical composition. The pharmaceutical composition of the active ingredient of this application may also include one or several pharmaceutically acceptable excipients, such as carriers, diluents, or excipients, and, optionally, other therapeutically active ingredient.

Pharmaceutical compositions suitable for parenteral administration also include injections, such as sterile solutions, suspensions, and emulsions, preferably sterile solutions. Pharmaceutical compositions suitable for oral administration include tablets, capsules, powder, granules, drop pills, paste, pulvis, tinctures, sustained release formulations, solutions, and suspensions, preferably tablets and capsules. wherein tablets can be ordinary tablets, dispersible tablets, effervescent tablets, sustained release tablets, controlled release tablets, or enteric-coated tablets; capsules can be ordinary capsules, sustained release capsules, controlled release capsules, or enteric-coated capsules.

The pharmaceutical compositions of this application can be prepared with conventional pharmaceutical excipients known in this field according to a conventional method. Conventional pharmaceutical excipients include fillers, absorbents, wetting agents, binders, disintegrants, lubricants, carriers, diluents, isotonic regulators, pH regulators, etc. Fillers mainly include starch, lactose, mannitol, and microcrystalline cellulose; absorbents mainly include calcium sulfate, calcium hydrogen phosphate, calcium carbonate, and magnesium oxide; wetting agents mainly include water and ethanol; binders mainly include hydroxypropyl methylcellulose, polyvidone, and microcrystalline cellulose; disintegrants include croscarmellose sodium, crospovidone, surfactant, and low-substituted hydroxypropyl cellulose; lubricants include magnesium stearate, talc, polyethylene glycol, magnesium lauryl sulfate, and micronized silica gel; carriers are selected from lactose, mannitol, trehalose, and glycine; diluents are selected from aqueous solvents (such as distilled water and/or sterile water for injection), optionally from bacteriostatic water for injection containing methylparaben and/or propylparaben and/or 0.9% benzyl alcohol, or optionally from normal saline (such as 0.9% sodium chloride solution, or 0.45% or 0.225% sodium chloride solution, or Ringer's solution, and/or lactated Ringer's solution); isotonic regulators are selected from glucose, sodium chloride, potassium chloride, and mannitol; pH regulators are selected from sodium hydroxide, ammonia, hydrochloric acid, sodium carbonate, sodium bicarbonate, dilute sulfuric acid, citric acid, sodium citrate, acetic acid, tartaric acid, sodium acetate, and disodium hydrogen phosphate. Pharmaceutical excipients also include colorants and sweeteners.

In a further aspect, this application provides a method of preventing or treating liver diseases, comprising administration of a therapeutically effective amount of the active ingredient of this application or their pharmaceutical composition to an individual in need thereof. In some embodiments, this method comprises administration of a therapeutically effective amount of the active ingredient of this application to an individual in need thereof.

In still another aspect, this application provides a use of the crystalline form A, crystalline form B, crystalline form C, crystalline form D, and crystalline form E and their crystalline composition or pharmaceutical composition in the preparation of a medicament for prevention or treatment of liver diseases.

In still a further aspect, this application provides a use of crystalline form A, crystalline form B, crystalline form C, crystalline form D, and crystalline form E and their crystalline composition or pharmaceutical composition for prevention or treatment of liver diseases.

In another aspect, this application provides a kit, which contains the active ingredient of this application or its pharmaceutical composition. In some embodiments, the kit also contains a instruction and a suitable package. In some embodiments, the instruction relates to a method of preventing or treating liver diseases (such as chronic viral hepatitis and/or acute drug-induced liver injury), comprising administration of a therapeutically effective amount of the active ingredient of this application to an individual in need thereof.

In some embodiments of any of the above aspects, the liver diseases include but not limited to chronic viral hepatitis and/or acute drug-induced liver injury.

It should be noted that, an XRD spectrum obtained from a crystalline compound is usually characteristic for a particular crystalline form, and the relative intensity of the spectral band may change due to the varying preferential orientation effect caused by differences in crystallization conditions, particle size, and other determination conditions. Thus, the relative intensity of diffraction peaks is not characteristic for a specific crystalline form; when judging whether it is the same as a known crystalline form, closer attention should be paid to the relative positions of peaks, instead of their relative intensity. In addition, for any given crystalline form, there may be slight errors in peak positions, which is well known in the field of crystallography. For instance, peak positions may change due to temperature change, sample movement, or instrument calibration in sample analysis. The error in 2θ measurement is usually ±0.2°. Thus, in determining the structure of a crystalline form, this error should be considered. In XRD spectra, usually angle 2θ or interplanar spacing d is used to represent peak positions, and there is a simple conversion relation between them: $d=\lambda/2 \sin \theta$, where d denotes interplanar distance, λ denotes incident wavelength of X-Rays, and θ denotes diffraction angle.

For the purpose of this application, "$X_{10}$" represents the particle diameter corresponding to 10% of the particle size distribution, in other words, cumulative 10% of the particles in all the tested particles are smaller than $X_{10}$; "$X_{50}$" represents the particle size corresponding to 50% of the particle size distribution, in other words, cumulative 50% of the particles in all the tested particles are smaller than $X_{50}$; "$X_{90}$" represents the particle size corresponding to 90% of the particle size distribution, in other words, cumulative 90% of the particles in all the tested particles are smaller than $X_{90}$.

Sv and Sm denote specific surface areas, i.e., total surface area of a material per unit volume (Sv) and total surface area of a material per unit of mass (Sm) respectively.

The term "individual" includes human beings, as well as animals, such as mammals (primates, cattle, horses, pigs, dogs, cats, mice, rats, rabbits, goats, sheep, poultry, etc.).

The term "optional" or "optionally" means that the event or situation described thereafter may or may not happen. That is, this description includes the circumstance where the event or situation occurs and the circumstance where the event or situation does not occur.

The crystalline form A, crystalline form B, crystalline form C, crystalline form D, and crystalline form E prepared according to this application has the advantage of high crystallinity, high purity, high stability, low hygroscopicity, or good fluidity, and are easy to reconstitution, and have a high clarity after reconstitution. They are particularly suitable for use in preparations for injection, and can overcome the defects of some properties of the compound of Formula I prepared according to the prior art, such as caking of the solid, difficult to filtrate, hard to dry, and poor clarity. They are also suitable for industrial production, and capable of improving product safety.

DETAILED DESCRIPTION OF THE EMBODIMENTS

The detailed examples are to illustrate the technical solution of this application, but not intended to limit the scope of this application in any way. All the reagents adopted are commercially available.

Instruments and Methods Used for Data Collection:

XRD spectra are measured under the following conditions using the instruments below: D/Max-RA Japan RigakuXMiniFlexII X-ray powder diffraction apparatus; Ray: monochromatic Cu-Kα ray (λ=1.5418 Å); scanning mode: θ/2θ; scanning range: 0~40°; voltage: 30 Kv; current: 15 mA; detection environmental conditions: temperature: 23.9° C.; humidity: 38.6%.

Thermogravimetric analysis (TGA) is performed under the following conditions using the instruments below: TG 209 F3 thermogravimetric analyzer; scanning rate: 10° C./min; scanning range: 30° C.~300° C.; protective gas: nitrogen.

The derivative thermogravimetry (DTG) curve is the first-order derivative curve of the TG curve relative to temperature. The relationship between the change rate of weight loss and temperature for samples is determined under isokinetic heating.

Water content is determined using the Karl-Fischer method.

Particle size distribution is determined according to the laser method using the instrument below: full-automatic dry-wet laser particle sizer, VIBRI (HELOSBR).

Example 1 Method of Preparing the Crystalline Form B

Figure 3:
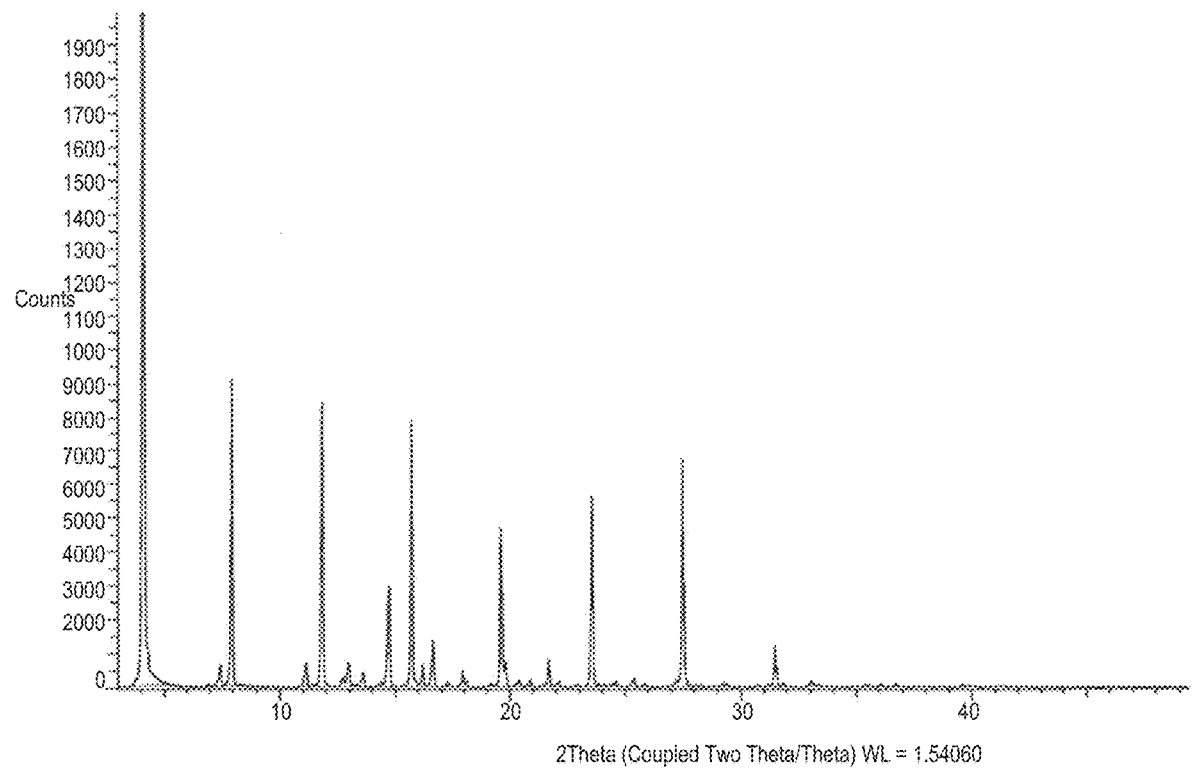

Weigh and take 15.0 g crude magnesium isoglycyrrhizinate, add 75 ml water and 75 ml anhydrous ethanol, heat the mixture until reflux, and stir under reflux until the solution is clear; filter the solution while hot, allow the filtrate to cool to 60~65° C., and maintain this temperature for 12 h; then cool it down to 40~45° C., and stir while crystallization for 6 h; further cool it down to room temperature, and stir while crystallization for 12 h; finally cool it down to 0~5° C., and stir while crystallization for above 12 h. Filter the filter cake, wash it twice using hydrous ethanol with 50% of volume fraction, and collect the filter cake to obtain the crystalline form B; using Cu-Kα radiation to obtain its XRD spectrum, as shown in FIG. 3.

Example 2 Method of Preparing Crystalline Form C

Figure 4:
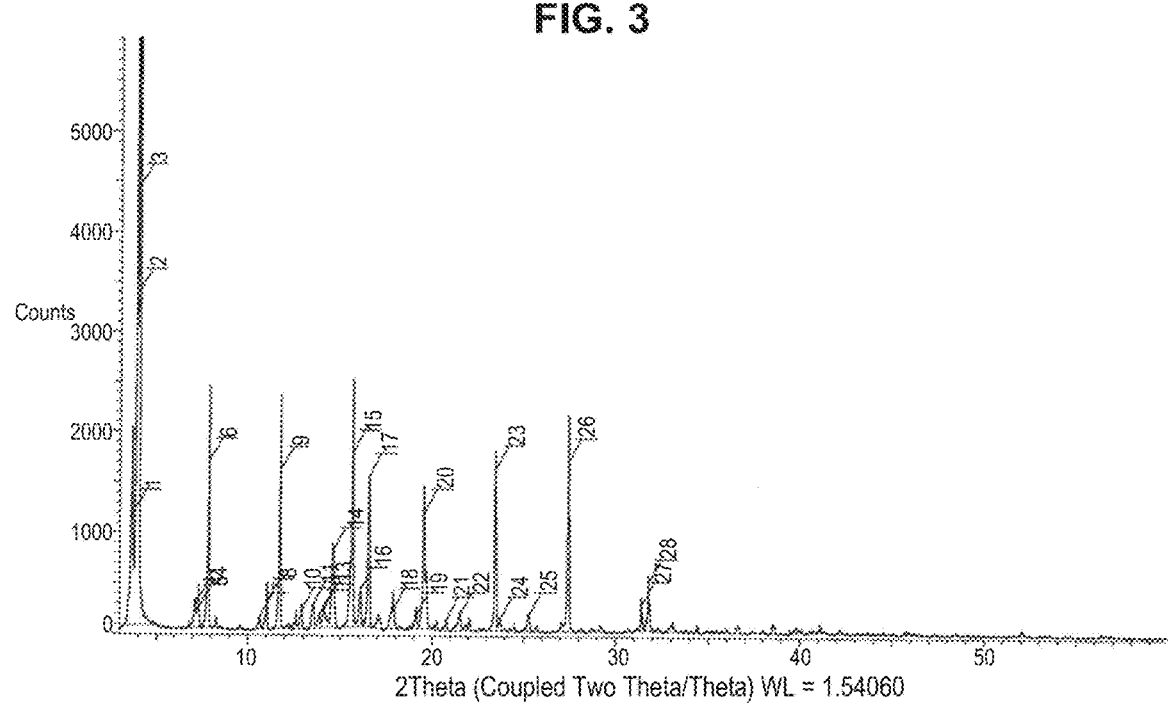

The filter cake obtained in example 1 is air-dried at 60° C. for 5 h to obtain the crystalline form C, water content (15.56%), and use Cu-Kα radiation to obtain XRD spectrum, as shown in FIG. 4.

Example 3 Method of Preparing Crystalline Form C

Figure 5:
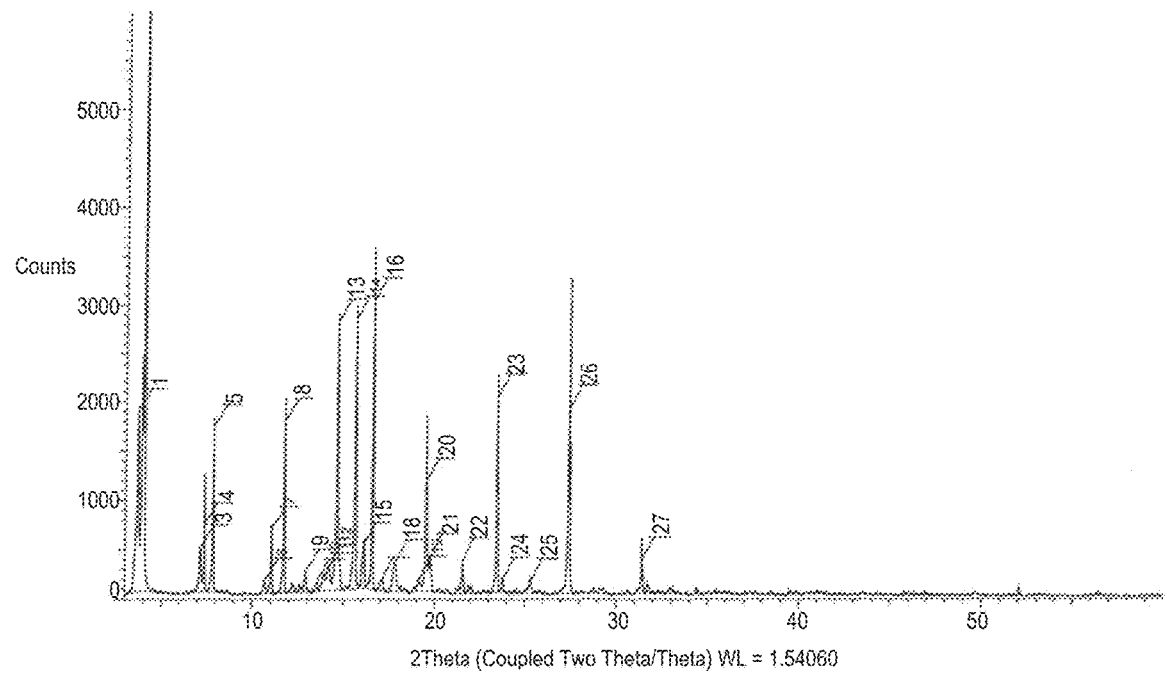

The filter cake obtained in example 1 is air-dried at 60° C. for 10 h to obtain the crystalline form C, water content (11.14%), and use Cu-Kα radiation to obtain its XRD spectrum, as shown in FIG. 5.

Example 4 Method of Preparing Crystalline Form D

Figure 6:
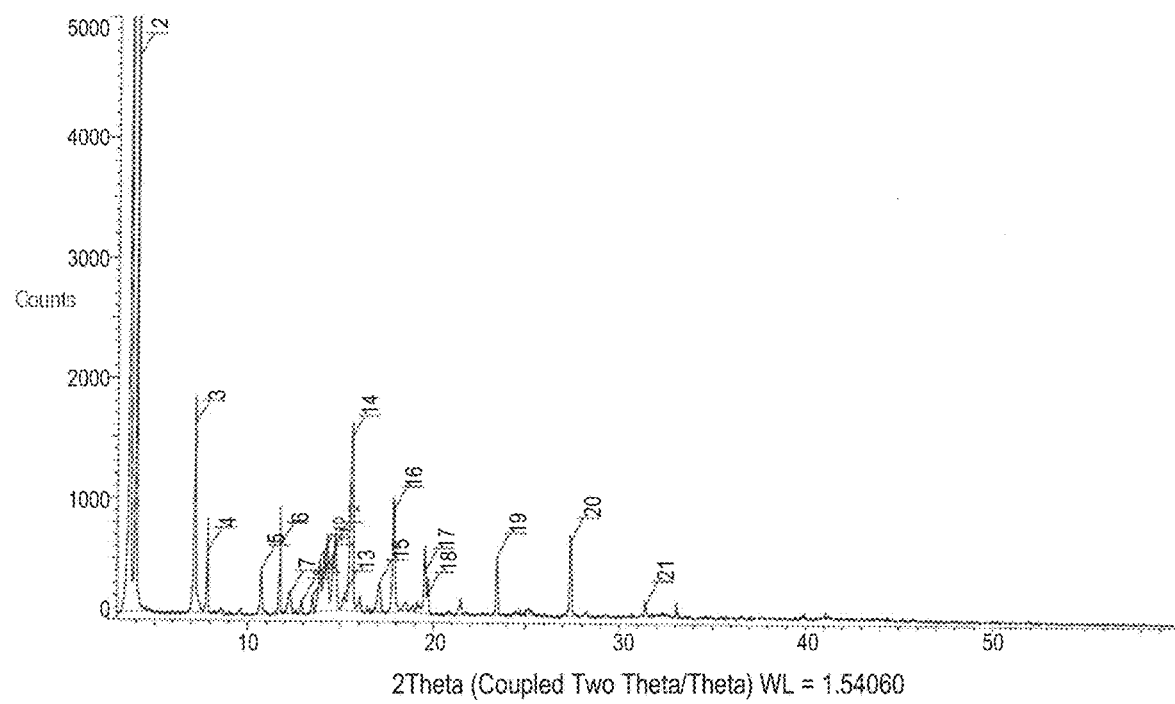

The filter cake obtained in example 1 is air-dried at 60° C. for 14 h to obtain the crystalline form D, water content (10.09%), and use Cu-Kα radiation to obtain its XRD spectrum, as shown in FIG. 6.

Example 5 Method of Preparing Crystalline Form A

Figure 1:
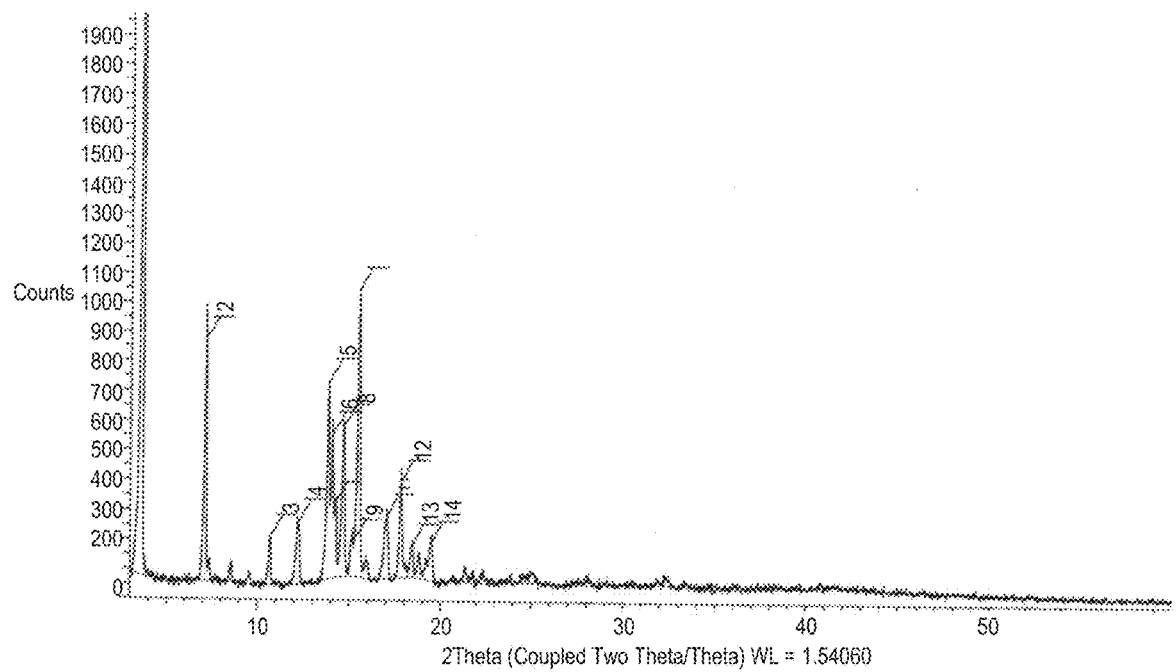
FIG. 1 XRD pattern of crystalline form A
FIG. 2 TG-DTG pattern of crystalline form A
FIG. 3 XRD pattern of crystalline form B
FIG. 4 XRD pattern of crystalline form C prepared in example 2
FIG. 5 XRD pattern of crystalline form C prepared in example 3
FIG. 6 XRD pattern of crystalline form D
FIG. 7 XRD pattern of crystalline form E
FIG. 8 Particle size distribution diagram of crystalline form A
Figure 2:
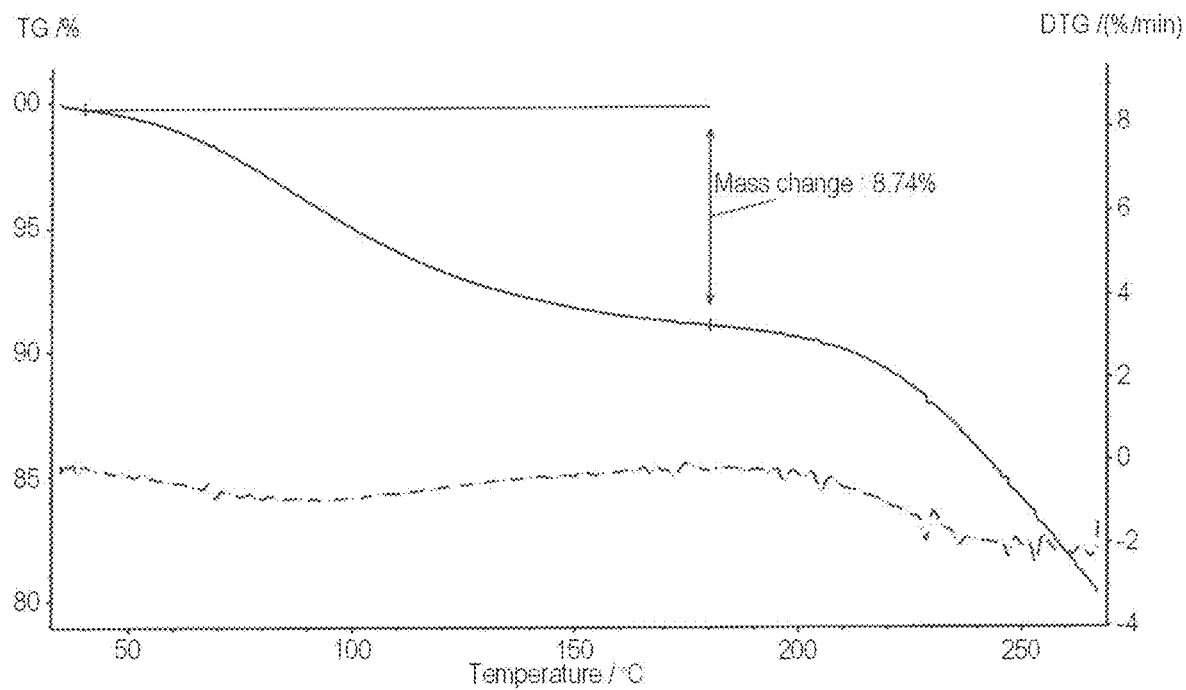

The filter cake obtained in example 1 is air-dried at 60° C. for 19 h to obtain the crystalline form A of magnesium isoglycyrrhizinate (12.6 g), water content (8.78%), and use Cu-Kα radiation to obtain its XRD spectrum, as shown in FIG. 1. FIG. 2 provides its TG-DTG spectrum, which shows a weight loss of 8.74% (about 4 moles of water).

Example 6 Method of Preparing Crystalline Form E

Figure 7:
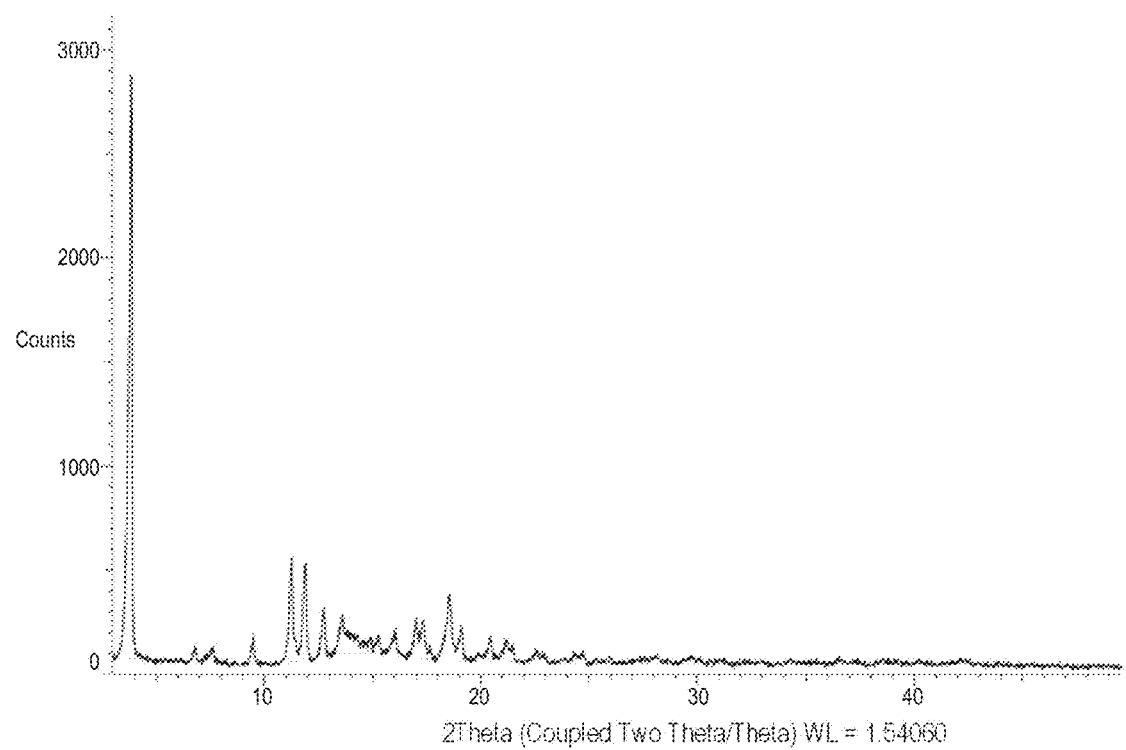

Weigh and take 20 g crude magnesium isoglycyrrhizinate, add 60 g isopropanol and 50 g water, heat the mixture until reflux, conduct heat-preservation stirring until the solution is clear; add activated carbon for decoloration, filter the solution while hot, cool the filtrate to 60~65° C., and stir while crystallization for 6 h; further cool it down to 40~45° C., and stir while crystallization for 6 h; further cool it down to room temperature, and stir while crystallization for 12 h. Finally cool it down to 0~5° C., and stir while crystallization for above 12 h. Filter the filter cake, wash it twice using isopropanol, and collect the filter cake (80 g), and dry it at 60° C. for 10~12 h to obtain the crystalline form E (16.8 g), and use Cu-Kα radiation to obtain its XRD spectrum, as shown in FIG. 7.

Example 7 Color and Clarity of Solution Test

"Color and clarity of solution test" is particularly important, and also a required inspection item for active ingredients used in preparations for injection. Weigh 0.5 g of the crystalline form A obtained in example 5, dissolve it with 10 ml dilute ammonia solution (1→100), and the solution may be clear and colorless. If the solution is colored, compare it with the yellow 2 #standard color solution (Method 1, General Principles 0901, the Chinese Pharmacopoeia), and the former should not be intensely colored than the latter. If the solution is turbid, compare it with the turbidity 0.5 #standard solution (Method 1, General Principles 0902, the Chinese Pharmacopoeia), and the former should not be more intensely turbid than the latter.

The results of color and clarity of solution test is as shown in Table 1 below:

TABLE 1

| Results of color and clarity of solution test | |
|---|---|
| color of solution test | clarity test |
| The solution is colorless, and less intensely colored than the yellow 2# standard color solution. | The solution is clear, and less intensely turbid than the turbidity 0.5# standard solution. |

Example 8 Measurement of Particle Size and Specific Surface Area

Figure 8:
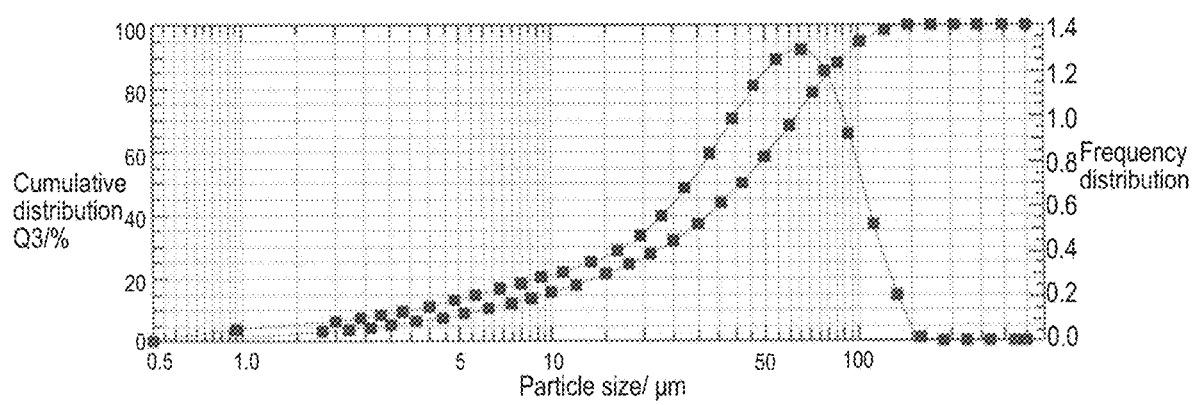

Take the crystalline form A obtained in example 5, measure its particle size and specific surface area, and the particle size distribution diagram is as shown in FIG. 8, and its particle size and specific surface area data are as shown in Table 2:

TABLE 2

| Measurement of particle size and specific surface area | | | | |
|---|---|---|---|---|
| $X_{10}$ | $X_{50}$ | $X_{90}$ | $S_v$ | $S_m$ |
| 6.19 μm | 42.18 μm | 91.80 μm | 0.44 m²/cm³ | 0.64 m²/g |

What is claimed:

1. Crystalline form A of a compound of Formula I,

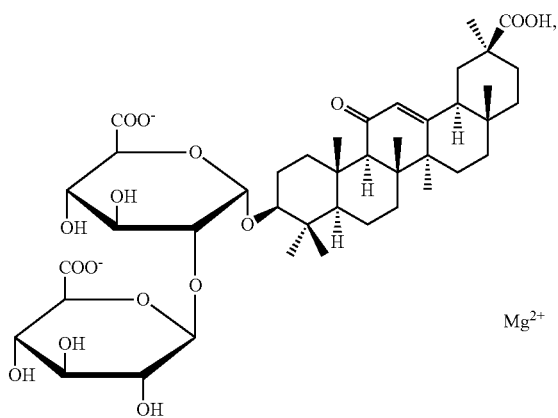

wherein the crystalline form A has an X-ray powder diffraction pattern comprising diffraction peaks at 2θ value of about 3.57°, 7.10°, 13.83°, 14.65°, and 15.48°.

2. The crystalline form A according to claim 1, wherein the crystalline form A has an X-ray powder diffraction pattern comprising diffraction peaks at 2θ value of about 3.57°, 7.10°, 12.20°, 13.83°, 14.65°, 15.48°, 17.00°, and 17.80°.

3. The crystalline form A according to claim 1, wherein the crystalline form A has an X-ray powder diffraction pattern comprising diffraction peaks at 2θ value of about 3.57°, 7.10°, 10.66°, 12.20°, 13.83°, 14.04°, 14.13°, 14.65°, 15.48°, 17.00°, 17.80°, and 19.46°.

4. The crystalline form A according to claim 1, wherein the crystalline form A has an X-ray powder diffraction pattern substantially as shown in FIG. 1.

5. The crystalline form A according to claim 1, wherein the crystalline form A contains from 7.0% to 10.0% water by weight.

6. The crystalline form A according to claim 1, wherein the crystalline form A contains from 7.7% to 8.8% water by weight.

7. The crystalline form A according to claim 1, wherein the crystalline form A is a tetrahydrate of the compound of Formula I.

8. A composition comprising above 50% by weight of the crystalline form A according to claim 1.

9. The composition according to claim 8, wherein the composition comprises above 70% by weight of the crystalline form A.

10. The composition according to claim 8, wherein the composition comprises above 90% by weight of the crystalline form A.

11. A pharmaceutical composition comprising the crystalline form A according to claim 1, and one or more pharmaceutically acceptable excipients.

12. A method of preventing or treating a liver disease in a subject, the method comprising administering a therapeutically effective amount of the crystalline form A according to claim 1 to the subject in need thereof.

13. The method according to claim 12, wherein the liver disease is at least one selected from the group consisting of chronic viral hepatitis and acute drug-induced liver injury.

14. The crystalline form A according to claim 1, wherein the crystalline form has a specific surface area of ≤0.1.0 m²/cm³.

15. The crystalline form A according to claim 14, wherein the crystalline form A has a specific surface area of about 0.4 m²/cm³.

16. The crystalline form A according to claim 14, wherein the crystalline form A has a specific surface area of <0.5 m²/cm³.

17. The crystalline form A according to claim 1, wherein the crystalline form A has a particle size distribution selected from the group consisting of:
(i) an $X_{10}$ value of about 3 to 10 μm, about 5 to 8 μm, or about 6 to 6.5 μm;
(ii) an $X_{50}$ value of about 30 to 55 μm, about 40 to 47 μm, or about 42 to 45 μm;
(iii) an $X_{90}$ value of about 80 to 120 μm, about 90 to 100 μm, or about 91 to 98.5 μm; and
(iv) any combination of two or more of (i), (ii), and (iii).

18. The crystalline form A according to claim 17, wherein the crystalline form A has a particle size distribution of an $X_{10}$ value of about 6 to 6.5 μm, an $X_{50}$ value of about 42 to 45 μm, and an X90 value of about 91 to 98.5 μm.

19. The crystalline form A according to claim 2, wherein the crystalline form A has a particle size distribution of an $X_{10}$ value of about 6 to 6.5 μm, an $X_{50}$ value of about 42 to 45 μm, and an X90 value of about 91 to 98.5 μm.

20. The crystalline form A according to claim 2, wherein the crystalline form A has a specific surface area of ≤0.5 m²/cm³.

* * * * *